United States Patent [19]

Kim

[11] 4,099,917

[45] Jul. 11, 1978

[54] PROCESS FOR PREPARING A CELL SUSPENSION FROM BLOOD FOR DISCRIMINATION OF WHITE BLOOD CELLS AND PLATELETS FROM OTHER BLOOD PARTICLES

[75] Inventor: Young Ran Kim, Hartsdale, N.Y.

[73] Assignee: Technicon Instruments Corporation, Tarrytown, N.Y.

[21] Appl. No.: 817,595

[22] Filed: Jul. 21, 1977

[51] Int. Cl.² ............................................ G01N 33/16
[52] U.S. Cl. .................................................. 23/230 B
[58] Field of Search ........................ 23/230 B; 195/1.8; 424/3

[56] References Cited

U.S. PATENT DOCUMENTS

| | | | |
|---|---|---|---|
| 3,741,875 | 6/1973 | Ansley et al. | 195/103.5 R |
| 4,040,785 | 8/1977 | Kim et al. | 23/230 B |

*Primary Examiner*—Robert M. Reese
*Attorney, Agent, or Firm*—Morgan, Finnegan, Pine, Foley & Lee

[57] ABSTRACT

Procedures are disclosed for obtaining white blood cell counts and platelet counts by light scattering measurements in which anticoagulated blood samples are treated such that the morphology of the white cells (leukocytes) and platelets remain intact and permit the discrimination of platelets from white cells and of most classes of white cells from one another and their counting without the need for staining.

11 Claims, No Drawings

PROCESS FOR PREPARING A CELL SUSPENSION FROM BLOOD FOR DISCRIMINATION OF WHITE BLOOD CELLS AND PLATELETS FROM OTHER BLOOD PARTICLES

BACKGROUND OF THE INVENTION

The existing methodology for platelet counting has not been entirely dependable. Automated versions of these methods have relied on chemistries which lead to platelet counts which are falsely elevated.

In typical platelet counting procedures, a material is added to a whole blood sample to lyse the red blood cells. Unfortunately, lysing procedures used up to the present time have had deleterious side-effects: material from the platelet themselves are extracted, some white blood cells are fragmented, and in some cases, protein precipitates are formed. When any of these occurrences takes place, the recorded platelet count is falsely elevated.

Regarding differential white blood cell count techniques presently available, it has not been possible to obtain leukocytes free from red blood cells by lysing without doing some concomitant damage to the leukocytes. Therefore, adequate differentiation of leukocytes as described in U.S. Pat. No. 3,741,875 is not possible unless the cells are stained by cytochemical reaction.

SUMMARY OF THE INVENTION

It is one object of this invention to make possible the discrimination of platelets from red cell ghosts and leukocytes as well as extracting platlet size information.

It is another object to make possible discrimination of most classes of unstained leukocytes by their size and granularity characteristics.

Accordingly, these objects are fulfilled by the process disclosed herein which is a process for preparing a cell suspension from a diluted blood sample for discrimination of white blood cells and platelets which comprises the steps of:

(a) treating an anticoagulated blood sample with a detergent which preconditions the red blood cells for subsequent lysing without damaging the white cell morphology;

(b) adding a fixative thereto with mixing while maintaining the mixture at a neutral pH; and (c) incubating at a temperature substantially from 55° C to 62° C for at least 2 minutes.

In a preferred embodiment, the detergent is polyoxyethylene 20 sorbitan monolaurate, and the incubation temperature is about 58° C and the incubation period is 2 minutes.

DETAILED DESCRIPTION OF THE INVENTION

In a continuous automated flow system apparatus such as the Hemalog D[1] which is designed to ease the burden of differential white blood cell counting and in the automated process described in U.S. Pat. No. 3,741,875, cytochemical procedures specifically identify and label individual cell types. The stream of stained and unstained cells flow through an optical view chamber where a photoelectric measuring process records the amplitudes of the light absorbed and separately, the light scattered by each cell. Electronic signals are sorted by amplitude and classified into categories corresponding to the several cell types. Data are printed for one sample/min. on the five major white cell types of whole blood. The specific chemical-identifying process stains the white blood cells. The light scattered roughly gauges the processed size of the cells.

[1] A Registered Trademark of Technical Instruments Corporation

The presently disclosed novel procedure for obtaining a differential white blood cell count is adaptable to both manual and automated techniques. In either case, the method allows for effective discrimination of most normal classes of unstained leukocytes by light scattering alone because the white cell morphology has not been damaged. The count is accurate as the cell preparation is free of any white cell clumps, red cell ghost clumps and platelet clumps.

One widely adopted methodology for platelet counting uses concentrated urea solution to lyse the red cells. This method also extracts some material from the platelets, fragments some white cells (producing particles that are indistinguishable from platelets in these instruments) falsely elevating the platelet count, and, with some abnormal bloods, causes the formation of very fine protein precipitates (which are also indistinguishable from platelets in these instruments) again falsely elevating the platelet counts in such bloods.

The extraction of platelet material by the urea lowers the refractility of the platelets which lowers the size of the scattered-light signal which they produce in these instruments. As a result, the smallest platelet signals merge with the largest system noise signals (produced by electronic noise in the detectors and amplifiers, and by the coincident passage through the photometric light-scattering detector of numbers or red cell ghosts, i.e., red cell membranes freed of their contents by lysis). It is therefore not possible to accurately set a threshold between the noise and platelets with great confidence.

The purpose of this invention is to provide a method which lyses the red cells without extracting material from the platelets, without fragmenting the white cells and without producing precipitates from the proteins of abnormal bloods. The described method produces pulse-height distribution of signals with a large well-defined minimum between noise and platelets as well as another large well-defined minimum between platelets and white cells.

The purpose of this invention is also to preserve the differences in white cell morphology which permit the discrimination of most classes of white cells from one another without staining.

The method of this invention, whether used for obtaining a differential white blood cell count or a platelet count, involves initially treating an anticoagulated blood sample with a detergent which preconditions the red blood cells for subsequent lysing.

The incorporation of detergent at this stage in the procedure is an important aspect of this invention. It acts as a preconditioner in that, at the concentrations added, it does not damage the morphology of the white blood cells or platelets nor lyse the red cells and yet prepares the red cells for subsequent lysing.

For purposes of this invention, the detergent is preferably polyoxyethylene 20 sorbitan monolaurate but other detergent materials, such as polyoxyethylene 23 monolaurylether and polyoxyethylene 20 sorbitan monooleate capable of preconditioning the red blood cells without lysing said red blood cells will be equally employable.

The concentration of detergent in the resulting mixture is between about 0.03 and 2.0% v/v and preferably from about 0.4 to about 0.6% v/v.

During the aforesaid preconditioning, the resulting mixture is permitted to incubate at room or ambient temperature, e.g., about 25° C for about one minute. This permits the detergent to satisfactorily carry out its designated function.

A fixative is added to the incubated mixture with agitation and the pH thereof is maintained at a neutral pH. Preferably, the fixative is a phosphate-buffered formaldehyde solution and the pH is in the range 6 to 8.

The mixture is then incubated at a temperature from about 55° C to about 62° C for at least 2 minutes, preferably for two minutes at 58° C.

At this point, the mixture is then diluted if necessary and measured optically. For platelet count determination, dilution is effected with an acidified isotonic saline solution and the resulting mixture has a pH from 2 to 4. A suspension using 0.5% acetic acid-saline provides an appropriate dilution, an improved platelet signal to noise ratio, a clean separation of platelets from red cell ghosts and leukocytes and the original individual platelet volumes are well preserved. It is also possible and in some instances preferred to partially dilute the sample by adding an isotonic saline solution prior to the detergent-treatment step.

For white blood cell determinations, the sample is diluted by the addition of an isotonic saline solution at least partially after the incubation step. Alternatively, the sample can be diluted at least partially prior to the detergent-treatment step.

The white blood cell suspension obtained from the above method diluted instead with an isotonic-saline solution retains the morphology of the white cells, allowing differentiation of unstained white cells by low- and high-angle light scatter, and permits the differentiation of lymphocytes, monocytes, neutrophils, and eosinophils without staining.

This method also preserves peroxidase activity of white cells permitting the further differentiation of two otherwise difficult to distinguish groups of leukocytes, peroxidase active and inactive agranulocytes.

The prepared suspension can be used on line for clinical hematology analysis by light scatter and it can be stored for use as reference for such a system.

EXAMPLE I

Macro Method

To an anticoagulated whole blood sample (0.1 ml) is added 0.32 ml of a 1% polyoxyethylene 20 sorbitan monolaurate solution (in isotonic saline) and the resulting mixture is permitted to incubate at room temperature for about one minute.

Phosphate-buffered formaldehyde solution (0.42 ml) containing 8% by volume formaldehyde is added to the mixture with stirring and the resulting mixture is incubated at 57° C for 2 minutes.

A. WHITE BLOOD CELL DETERMINATION

To the above incubated mixture is added isotonic saline (1.2 ml) and the white blood cell differential count is measured by light scatter.

B. PLATELET DETERMINATION

To the above incubated mixture is added isotonic saline (1.2 ml). 0.1 ml of the resulting mixture is added to 4.0 ml of a 0.5% acetic acid-isotonic saline solution. The platelet count and size measurements are effected by light scatter.

EXAMPLE II

Micro Method METHOD 0.01 ml of anticoagulated capillary whole blood is diluted at a ratio of 1:10 with an isotonic saline solution and the 0.1 ml of the resulting mixture is added to 0.32 ml of a 0.125% polyoxyethylene 20 sorbitan monolaurate solution (in isotonic saline) and the resulting mixture is allowed to incubate at room temperature for about one minute.

Phosphate-buffered formaldehyde solution (0.42 ml) containing 8% by volume formaldehyde is added to the mixture while agitating and the resulting mixture is incubated at 57° C for 2 minutes.

A. WHITE BLOOD CELL DETERMINATION

The white blood cell differential count of the above suspension is measured by light scatter.

B. PLATELET DETERMINATION

To the above incubated mixture is added isotonic saline (1.2 ml). 0.1 ml of the resulting mixture is added to 1.0 ml of a 0.5% acetic acid-isotonic saline solution. The platelet count and size measurements are effected by light scatter.

It should be understood by those skilled in the art that various modifications may be made in the present invention without departing from the spirit and scope thereof as described in the specification and defined in the appended claims.

What is claimed is:

1. A process for preparing a cell suspension from a diluted blood sample for discrimination of white blood cells and platelets from other blood particles which comprises the steps of:
    (a) treating an anticoagulated blood sample with a detergent which preconditions the red blood cells for subsequent lysing without damaging the white cell morphology;
    (b) adding a fixative thereto with mixing while maintaining the mixture at a neutral pH; and
    (c) incubating at a temperature substantially from 55° C to 62° C for at least 2 minutes.

2. The process of claim 1 wherein said detergent is polyoxyethylene 20 sorbitan monolaurate present in amounts to provide a concentration of from 0.3 to 2.0% v/v in the mixture.

3. The process of claim 1 wherein step (a) includes the step of incubating the detergent-treated blood sample at room temperature for about 1 minute.

4. The process of claim 1 wherein the mixture in step (b) after addition of fixative is maintained at a pH of from 6 to 8.

5. The process of claim 1 wherein said fixative is a phosphate-buffered formaldehyde solution.

6. The process of claim 1 wherein the temperature of step (c) is about 58° C and the incubation period is 2 minutes.

7. The process of claim 1 for white blood cell determination wherein said dilution of sample is effected at least partially after the incubation step (c) using an isotonic saline solution and the resulting mixture has a pH from 6 to 8.5.

8. The process of claim 1 for white blood cell determination wherein said dilution of sample is effected at least partially prior to the detergent treatment of step (a).

9. The process of claim 1 for platelet counting wherein said dilution of sample is effected after incubation step (c) using an acidified isotonic saline solution and the resulting mixture has a pH from 2 to 4.

10. The process of claim 9 wherein said isotonic saline is acidified by addition of acetic acid.

11. The process of claim 9 wherein dilution of sample is effected partially by addition of isotonic saline solution prior to the detergent treatment of step (a).

* * * * *